United States Patent [19]

Bisping

[11] Patent Number: 4,886,074

[45] Date of Patent: Dec. 12, 1989

[54] IMPLANTABLE LEAD ASSEMBLY WITH EXTENDABLE SCREW-IN ELECTRODE

[76] Inventor: Hans-Jürgen Bisping, Am Lütterbüschgen 12, 5100 Aachen, Fed. Rep. of Germany

[21] Appl. No.: 167,890

[22] Filed: Mar. 14, 1988

[51] Int. Cl.⁴ .............................................. A61N 1/05
[52] U.S. Cl. .................... 128/785; 128/786; 128/419 P
[58] Field of Search .................... 128/784-786, 128/642, 419 P

[56] References Cited

U.S. PATENT DOCUMENTS

| 4,106,512 | 8/1978 | Bisping | 128/419 P X |
| 4,217,913 | 8/1980 | Dutcher | 128/785 |
| 4,381,013 | 4/1983 | Dutcher | 128/785 |

FOREIGN PATENT DOCUMENTS

| 2949782 | 6/1981 | Fed. Rep. of Germany | 128/785 |
| 3020584 | 12/1981 | Fed. Rep. of Germany | 128/785 |

Primary Examiner—Lee S. Cohen
Attorney, Agent, or Firm—Watson, Cole, Grindle & Watson

[57] ABSTRACT

An implantable electrode type lead assembly of the flexible type which is particularly adapted for implantation in the cardiac muscle for applications such as use with a pacemaker. The lead assembly has an electrode head which includes a fixation spiral for implantation into tissue and as well as a blocking mechanism. The electrode head includes all of the elements required for the blocking function of the mechanism and can be released by axial movement of the fixation spiral or of a connector block associated with the spiral.

8 Claims, 2 Drawing Sheets

IMPLANTABLE LEAD ASSEMBLY WITH EXTENDABLE SCREW-IN ELECTRODE

BACKGROUND OF THE INVENTION

This present invention relates to a lead assembly including an electrode which is adapted for connecting a living organ to an electrical device. In one embodiment, the subject invention is adaptable for a pacing and sensing lead assembly which is transvenously implantable for connecting a heart pacemaker device and cardiac tissue.

In pacemaker technology and related arts, a body implanted, intravascular lead assembly is oftentimes used which comprises an electrical conductor which, at its distal end, is adapted to be suitably connected to a source of electrical energy. The assembly further includes an electrode means at the other end of the conductor which is adapted to be secured to tissue. With pacemakers, an intravenous transplantation method may be utilized to install the lead assembly. With this method, which may be made under local anesthesia, the electrode means is pushed into the heart through a vein.

In a typical lead assembly for use in the above purposes, the lead assembly of an electrical conductor and electrode means affixed to the end of the conductor is adapted to be firmly lodged in and permanently secured to or removeable from tissue inside the body at a desired location. The conductor and the portion of the electrode means affixed to the conductor are sealed from body fluids and tissue by a material substantially inert to body fluids and tissue. Sheath means are provided for permitting the lead and electrode means to be inserted into and guided through a body vessel to a position inside the body without causing injury to the body vessel and for permitting the electrode means to be firmly lodged in and permanently secured to body tissue. The electrode of the lead assembly may be firmly anchored to tissue such as the heart muscle by mechanical fixation devices such as metal or plastic hooking devices and, in one known embodiment, by a helix of suitable electrode material within the sheath of the lead assembly.

A typical lead assembly for the above-mentioned purposes is exemplified in DE-05 30 20 584 and this assembly includes a blocking mechanism which blocks the store by means of an additional blocking wire or thread. Such a blocking wire or thread may be operated from the distal end of the lead assembly and unlocked by being pulled out of the electrode lead. Such a blocking wire or thread is difficult to use since space required for this purpose is not available.

Another lead assembly as is disclosed in U.S. Patent No. 4,106,512 to Bisping, incorporated by reference herein in its entirety, has a flexible helical conductor whose end has a lapse helix. Force exerted from the proximal end causes axial movement such that the conductor can be either extracted from or screwed into the tissue. With this type of lead assembly where the forces must be exerted from the proximal end, difficulties may be encountered in that, due to the tension forces along the electrical conductor and the insulating sheath, dislocation of the electrode head can occur during fixation of the conductor. Manipulation of the electrode head during fixation is, of course, not particularly desireable.

SUMMARY OF THE INVENTION

It is therefore a feature of the subject invention to provide an improved lead assembly having a blocking device and store which only require a simple, precise release of the blocking mechanism which allows the exertion of very small forces to complete such a release.

Another feature of the invention is to provide a lead assembly having a blocking mechanism which may be released by axial movement of and its (fixation spiral) connector block within the electrode lead and its insulating sheath.

In accordance with the invention, all the elements of the blocking mechanism are directly attached to the fixation sprial, the connector block, the electrode lead or the insulating sheath such that release of the block is accomplished by axial movement of the spiral and the connector block from the area of the blocking mechanism at the electrode head or the insulating sheath. With such a design for the blocking mechanism, small axial forces are sufficient to release the blocking mechanism and axial movement of the fixation spiral or the connector block can be accomplished either mechanically, hydraulically or pneumatically, e.g., by means of carbonic acid.

Mechanical release of the blocking mechanism can be simply accomplished by means of an axial shifting movement of a stylet. Such stylets are usually introduced into the interior of the electrode lead in order to ensure a stabilization of the electrode lead during the implantation phase. The stylet, which is available in the process anyway, can therefore be used to release the blocking mechanism.

Preferred embodiments for blocking mechanisms according to the invention have form-fitting interlocking connector elements at the fixation spiral or the connector block and the electrode head or the insulating sheath, the end of the connector block opposed from the fixation spiral being particularly suited to accommodate the blocking mechanism.

In various embodiments, the blocking mechanism can be formed of a groove and a pin, of a saw-tooth-shaped recess and a pin as well as of matching saw-tooth-shaped recesses and projections. Furthermore, other form-fitting connections, such as radially interlocking wedge profiles, can be used.

In these blocking mechanisms, the axial force required for the removal of the blocking mechanism can be adjusted as required by appropriate inclination of the contact surfaces relative to each other. Preferably the inclination of the contact surfaces is adjusted so as to ensure that only deliberate release of the blocking mechanism is possible and that unintentional self-release is virtually impossible. It is preferred that the contact surfaces of the blocking mechanism are inclined such that they obstruct the release of the blocking mechanism, the blocking elements thereby producing a latching effect in connection with the torsion tension of the store. In order to provide a safe and effective connection between the guiding device or the guiding pin and the fixation spiral after the blocking mechanism has been released it is preferable to harmonize the axial extension of the fixation spiral or the connector block and the axial extension of the blocking mechanism as well as the position of the guiding device or the guiding pin such that the guiding pin interlocks with the fixation spiral after the blocking mechanism is released. In comparison with other common guiding means, the guiding pin provides the advantage that it ensures a reliable interlock with the fixation spiral while generating only small frictional forces.

In a preferred embodiment, the electrode lead conductor is shaped as a store and thus a non-rotatable connection of the electrical conductor is possible in any position of the insulating sheath. If the electrical conductor is secured to the insulating sheath at the proximal end of the electrode head such that it is non-rotatable but is releasable, for example, by means of a stud bolt, the torsional tension can be applied from the proximal end either before implantation of the lead assembly or during implantation. If the mechanism preventing rotation is fastened in any place of the insulating sheath and is not accessible from the exterior, the torsional tension can be applied from the electrode head by inserting a turning type tool into an access opening at the fixation spiral or the connector block. In a preferred embodiment where means are provided to prevent an unintentional release of the blocking mechanism during implantation, the stylet is secured against an unintentional forward shift by provided a securing element at the proximal end of the stylet.

Further features of the present invention are illustrated in the accompanying drawings which show several embodiments according to the invention.

DETAILED DESCRIPTION OF THE PREFERRED EMBODIMENTS

Figure 3:
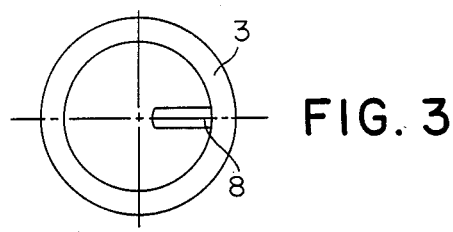
FIG. 3 is an end view of the electrode head shown in FIG. 1.
Figure 1:
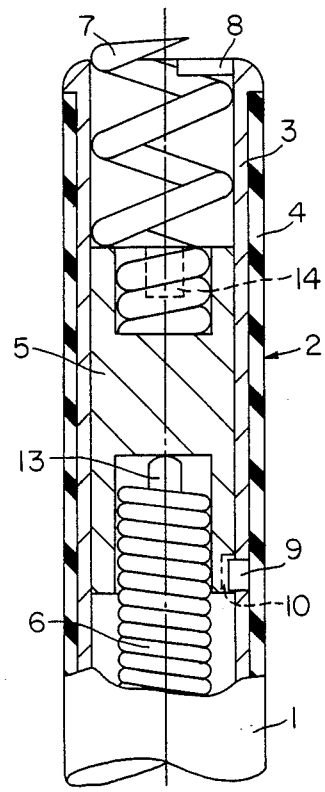
FIG. 1 is a side view of the distal end of an electrode lead assembly according to the invention, the view being partially in section with the fixation spiral or connector block being shown in its blocked position.
Figure 2:
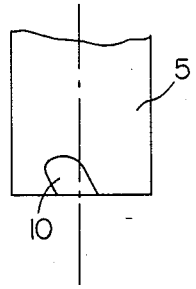
FIG. 2 is a partial side view of the connector block of FIG. 1.

Referring first to FIG. 1, the lead assembly of the invention has distal end 1 of electrode lead 2 which includes electrically conducting sleeve 3 shaped as a contact surface at the distal end of the head. Electrically conducting sleeve 3 is surrounded by electrically insulating sheath 4. Located within sleeve 3 is axially shiftable connector block 5 which is, on one end, connected with electrical conductor coil 6 and, on the distal end, is connected to fixation spiral 7. Connector block 5 is guided within sleeve 3 by sealing rings not shown which may be of an electrically conductive material so as to insure good electrical contact between conductor 6, sleeve 3 and fixation spiral 7. At the distal end of sleeve 3 is fastened guiding pin 8 which projects into the interior of the sleeve. Projecting inwardly from sleeve 3 is additional pin 9 which, in the blocking position of FIG. 1, interlocks with groove 10 in connector block 5 and thereby prevents rotary movement of the block as is shown in FIG. 1. In the blocking position of FIG. 1, a turn of spiral 7 is spaced inwardly from pin 8 a short distance to allow block 5 to be axially shifted, initially, in the direction of the arrow of FIG. 1 enough to release the block from pin 9. Thus, when block 5 is axially shifted in such direction, the spiral turn contacts pin 8, the block is released from pin 9 and the stored torsional force of conductor 6 causes spiral 7 to rotate while threading through pin 8

Figure 6:
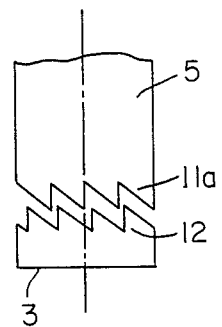
FIG. 6 is a partial side view of yet another embodiment of a connector block according to the invention.
Figure 4:
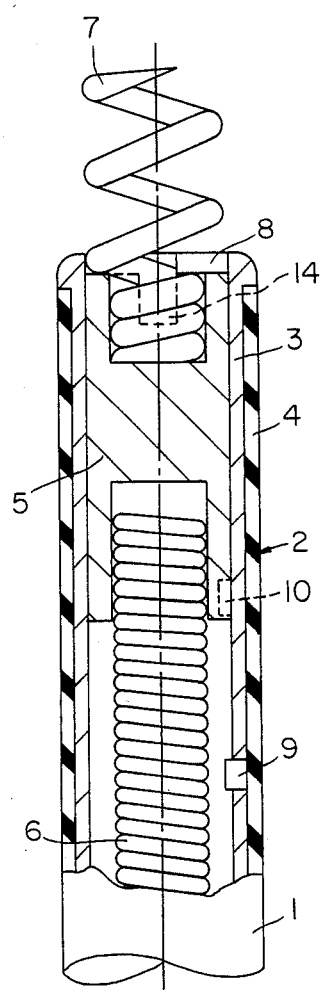
FIG. 4 is a side view, partially in section, of the distal end of an electrode lead assembly as is shown in FIG. 1 but where the fixation spiral or connector block has been released from the block.
Figure 5:
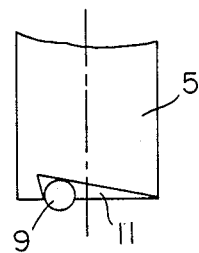
FIG. 5 is a partial side view of another embodiment of a connector block where a pin is attached to the electrode head.

Alternatively, rotation of block 5 can be prevented by the embodiments illustrated in FIGS. 5 and 6. In FIG. 5, pin 9 of sleeve 3 interlocks with saw-toothed-shaped recess 11 in connector block 5 so as to insure against rotary movement. In the embodiment of FIG. 6, the blocking mechanism comprises a plurality of saw-toothed-shaped recesses 11a in connector block 5 and complementary recesses 12 in sleeve 3 or an ancillary element of the sleeve.

Referring back to FIG. 1, stylet 13 is located within electrical conductor 6 and has its frontal surface in contact with connector block 5. If an axial force in the direction of the arrow towards the distal end 1 of electrode head 2 is applied to stylet 13, the stylet will shift connector block from its blocking position. As a consequence, the torsional force of electrical conductor 6 forces connector block 5 and thus fixation spiral 7 to rotate which, by the contact with guide pin 8, causes the spiral to extend or screw outwardly from the distal end of the electrode head 1.

At the distal end of connector block 5 is access opening 14 adapted to receive a turning tool (not shown) which enables the electrical connector to be placed under increased tension.

While there has been shown and described what is considered to be preferred embodiments of the present invention, it will be apparent to those skilled in the art that various changes and modifications may be made therein without departing from the invention as defined in the appended claims.

It is claimed:

1. A body-implantable, flexible lead assembly for electrical transmission to body tissue, comprising an electrode head open at one end, said head including an outer electrical insulating sheath, an axially shiftable connector block within said head, a fixation spiral connected to said block and having a tissue engaging end extending partially through said one end in a retracted, blocking position of said block, said head having a guiding device at said one end, a torsionally wound electrical coil conductor connected to said block, said coil having torsionally stored energy in said blocking position, a releasable blocking mechanism acting between said head and one of said block and said fixation spiral for retaining said spiral in said retracted, blocking position, a turn of said spiral being inwardly spaced a predetermined distance from said guiding device in said block position, and said blocking mechanism being movable to a release position for unblocking said spiral upon said block being axially shifted manually through said predetermined distance toward said one end, whereby upon unblocking said spiral turn engages said guiding device and threads further through said one end while rotating upon release of the torsionally stored energy of said coil.

2. The lead assembly according to claim 1, wherein said blocking mechanism comprises cooperating elements at least one of which is inclined in a direction opposite the torsionally wound direction of said coil to avoid unintentional release of said elements.

3. The lead assembly according to claim 2, wherein said cooperating elements comprise an inclined groove and a blocking pin.

4. The lead assembly according to claim 2, wherein said cooperating elements comprise inclined sawtooth-shaped recesses.

5. The lead assembly according to claim 2, wherein said cooperating elements comprise an inclined recess and a blocking pin.

6. The lead assembly according to claim 2, wherein one of the connector block and the fixation spiral has an access opening for the reception of a turning tool for torsionally winding the coil.

7. The lead assembly according to claim 1, further comprising an axially shiftable stylet extending through said coil and bearing against said block for manually moving said block to said release position.

8. The lead assembly according to claim 1, wherein said guiding device comprises a radially extending guide pin.

* * * * *